(12) United States Patent
Unger et al.

(10) Patent No.: US 12,671,453 B2
(45) Date of Patent: Jun. 30, 2026

(54) TWO-WAY RADIO DEVICE FOR HEARING PROTECTION DEVICES

(71) Applicant: Good Sportsman Marketing, LLC, Irving, TX (US)

(72) Inventors: Howard Unger, Henderson, NV (US); Daniel Dvorak, Henderson, NV (US); Dillon Douglas, Henderson, NV (US)

(73) Assignee: Good Sportsman Marketing, LLC, Irving, TX (US)

( * ) Notice: Subject to any disclaimer, the term of this patent is extended or adjusted under 35 U.S.C. 154(b) by 235 days.

(21) Appl. No.: 18/618,217

(22) Filed: Mar. 27, 2024

(65) Prior Publication Data

US 2024/0267070 A1    Aug. 8, 2024

Related U.S. Application Data

(63) Continuation-in-part of application No. 17/949,110, filed on Sep. 20, 2022, now Pat. No. 12,226,286, (Continued)

(51) Int. Cl.
| | |
|---|---|
| *H04B 1/3827* | (2015.01) |
| *A61F 11/14* | (2006.01) |
| *H04R 1/10* | (2026.01) |

(52) U.S. Cl.
CPC .............. *H04B 1/385* (2013.01); *A61F 11/14* (2013.01); *H04R 1/1008* (2013.01); *H04R 1/1041* (2013.01); *H04R 1/105* (2013.01); *H04R 1/1075* (2013.01); *H04R 1/1083* (2013.01); *H04B 2001/3866* (2013.01); *H04R 2201/107* (2013.01); *H04R 2420/07* (2013.01); *H04R 2460/01* (2013.01)

(58) Field of Classification Search
None
See application file for complete search history.

(56) References Cited

U.S. PATENT DOCUMENTS

| | | | |
|---|---|---|---|
| 2,235,372 A | 3/1941 | Kalbitz | |
| 3,306,991 A | 2/1967 | Wood | |
| | (Continued) | | |

FOREIGN PATENT DOCUMENTS

| | | | | |
|---|---|---|---|---|
| CN | 109314812 A | * | 2/2019 | .......... H04R 1/1066 |
| CN | 214967652 U | | 12/2021 | |
| | (Continued) | | | |

OTHER PUBLICATIONS

Office Action in U.S. Appl. No. 17/949,110 mailed Aug. 2, 2024, 19-pgs.

*Primary Examiner* — Mohammed Rachedine
(74) *Attorney, Agent, or Firm* — Cabello Hall Zinda, PLLC

(57) ABSTRACT

A two-way radio device for hearing protection devices provides communication capabilities to users wearing hearing protection devices, which would ordinarily hinder or block communication. The two-way radio device removably attaches to a portion of a hearing protection device and connects to the speakers thereof. One or more wireless transceivers provide wireless transmission of audio between users of hearing protection devices enhanced with the two-way radio device. Users remain protected by their hearing protection devices and while communicating freely in high decibel environments.

25 Claims, 14 Drawing Sheets

Related U.S. Application Data which is a continuation-in-part of application No. 16/530,722, filed on Aug. 2, 2019, now Pat. No. 11,451,900.

(60) Provisional application No. 62/717,809, filed on Aug. 11, 2018.

(56) References Cited

U.S. PATENT DOCUMENTS

| | | | |
|---|---|---|---|
| 4,905,322 | A | 3/1990 | Aileo et al. |
| 5,469,505 | A | 11/1995 | Gattey et al. |
| 5,835,609 | A | 11/1998 | LeGette et al. |
| 5,862,241 | A | 1/1999 | Nelson |
| 6,430,299 | B1 | 8/2002 | Hall et al. |
| 7,171,698 | B2 | 2/2007 | Saffran |
| 8,213,667 | B2 | 7/2012 | Nelson et al. |
| 8,488,814 | B2 | 7/2013 | Robuchon et al. |
| 9,445,182 | B2 | 9/2016 | Pizzaro et al. |
| 9,641,926 | B2 | 5/2017 | Awiszus et al. |
| 10,154,335 | B1 | 12/2018 | Hoang |
| 10,567,860 | B2 | 2/2020 | Han |
| 10,779,071 | B2 | 9/2020 | Wu |
| 11,477,575 | B2 | 10/2022 | Degner et al. |
| 11,736,855 | B1 | 8/2023 | Xu |
| 2009/0323975 | A1* | 12/2009 | Groesch ............... H04R 1/1091 |
| | | | 381/71.1 |
| 2011/0026726 | A1 | 2/2011 | Kuo |
| 2011/0051976 | A1 | 3/2011 | Tsai |
| 2014/0321658 | A1 | 10/2014 | Rahangdale |
| 2015/0222980 | A1* | 8/2015 | Pizzaro ................ H04R 1/1075 |
| | | | 381/371 |
| 2018/0176673 | A1 | 6/2018 | Madsen et al. |
| 2018/0338201 | A1 | 11/2018 | Mann |
| 2021/0260414 | A1 | 8/2021 | Mundy et al. |
| 2022/0353596 | A1 | 11/2022 | Kuraoka et al. |
| 2023/0030946 | A1* | 2/2023 | Warren .................... H04R 1/10 |

FOREIGN PATENT DOCUMENTS

| | | | | |
|---|---|---|---|---|
| CN | 114564103 | A | 5/2022 | |
| EP | 3337181 | A1 | 6/2018 | |
| EP | 4380184 | A1 * | 6/2024 | ............... H04R 3/12 |
| GB | 1376455 | A | 12/1974 | |
| GB | 2586915 | A | 3/2021 | |
| WO | 9530221 | A1 | 11/1995 | |
| WO | 2008122081 | A1 | 10/2008 | |
| WO | WO-2017205107 | A1 * | 11/2017 | ............... H04R 5/04 |

* cited by examiner

TWO-WAY RADIO DEVICE FOR HEARING PROTECTION DEVICES

CROSS-REFERENCE TO RELATED APPLICATION

This application is a continuation-in-part of U.S. patent application Ser. No. 17/949,110, filed Sep. 20, 2022, which is a continuation-in-part of U.S. patent application Ser. No. 16/530,722, filed Aug. 2, 2019, which claims priority to U.S. Provisional Patent Application No. 62/717,809, filed Aug. 11, 2018.

FIELD OF THE DISCLOSURE

The subject matter of the present disclosure relates to communication transceivers and in particular to a two-way radio device for hearing protection devices.

BACKGROUND OF THE DISCLOSURE

Personal protective equipment, such as earmuffs or earplugs, are recommended for use in environments where people are exposed to harmful or potentially harmful decibel levels. In general, this equipment protects users by providing a barrier which reduces the level of noise or other sounds that are able to reach the users' ears. For instance, sound may be attenuated by covering the entire ear or by an insert placed in the ear canal.

From the discussion that follows, it will become apparent that the subject matter of the present disclosure addresses the deficiencies associated with the prior art while providing numerous additional advantages and benefits not contemplated or possible with prior art constructions.

SUMMARY OF THE DISCLOSURE

In one configuration, a communication device disclosed herein is for use with a hearing protection device. The hearing protection device has a cup and a first electronic connector, and the cup has an inner side and an outer side. The outer side has first and second portions, and the inner side has a speaker in electronic communication with the first electronic connector. The communication device comprises an enclosure, a first arm, a second arm, and a latch.

The enclosure has a mounting side, a first end, a second end, audio communication circuitry, and a second electronic connector. The mounting side is configured to position adjacent to the outer side of the cup, and the audio communication circuitry is in electronic communication with the second electronic connector. The second electronic connector is configured to connect to the first electronic connector of the hearing protection device.

The first arm is disposed toward the first end of the enclosure. The first arm extends from the mounting side and is configured to mount to the first portion of the cup in a first removable attachment. The first arm is movable between first and second states relative to the enclosure. The second arm is disposed toward the second end of the enclosure. The second arm extends from the mounting side and is configured to mount to the second portion of the cup in a second removable attachment. The latch is arranged between the enclosure and the first arm and is movable between first and second conditions. The latch in the first condition is configured to engage the first arm in at least the first state, and the latch in the second condition is configured to disengage from the first arm.

In another configuration, a communication device is used for use with a hearing protection device. The hearing protection device has a cup and a first electronic connector. The cup has an inner side and an outer side, and the outer side has first and second portions. The inner side has a speaker in electronic communication with the first electronic connector. The communication device comprises an enclosure, a first arm, a second arm, and a latch.

The enclosure has a mounting side, a first end, a second end, audio communication circuitry, and a second electronic connector. The mounting side is configured to position adjacent to the outer side of the cup, and the audio communication circuitry is in electronic communication with the second electronic connector. The second electronic connector is configured to connect to the first electronic connector of the hearing protection device.

The first arm is disposed toward the first end of the enclosure. The first arm extends from the mounting side and is configured to mount to the first portion of the cup in a first removable attachment. The first arm defines first and second engageable slots, and the first arm is movable between first and second states relative to the enclosure. The second arm is disposed toward the second end of the enclosure. The second arm extends from the mounting side and is configured to mount to the second portion of the cup in a second removable attachment. The latch is arranged between the enclosure and the first arm and is movable between first and second conditions. The latch has a key. When in the first condition, the key on the latch is configured to engage the first and second engageable slots of the first arm in the first and second states. The key on the latch in the second condition is configured to disengage from the first and second engageable slots of the first arm.

An assembly disclosed herein includes a hearing protection device and a communication device. The hearing protection device has a headband, a cup, and a first electronic connector. The cup has an inner side and an outer side. The outer side has first and second portions, and the inner side has a speaker in electronic communication with the first electronic connector. The communication device can be arranged according to the configurations disclosed above and can be configured to removably mount on the cup.

The foregoing summary is not intended to summarize each potential embodiment or every aspect of the present disclosure.

BRIEF DESCRIPTION OF DRAWINGS

The components in the figures are not necessarily to scale, emphasis instead being placed upon illustrating the principles of the present disclosure. In the figures, like reference numerals designate corresponding parts throughout the different views.

FIGS. 18A-18O illustrate schematic views of the function of the clamping arm of the disclosed communication device;

FIG. 19 illustrates a schematic view of a latch profile for the disclosed communication device;

FIGS. 20A-20B illustrate additional schematic views of the function of the clamping arm of the disclosed communication device.

DETAILED DESCRIPTION OF THE DISCLOSURE

In the following description, numerous specific details are set forth in order to provide a more thorough description of the present disclosure. It will be apparent, however, to one skilled in the art, that the present disclosure may be practiced without these specific details. In other instances, well-known features have not been described in detail so as not to obscure the disclosed subject matter.

It is often difficult to communicate when hearing protection devices are adorned. Users often resort to raising their voices or partially or completely removing their hearing protection in order to communicate with other people. This is inconvenient and undesirable in terms of hearing protection. Moreover, vocal communication is limited to the range a user's voice or other audible communication can travel.

In general, the communication device disclosed herein adds communication capabilities to hearing protection devices. This permits users to communicate with one another while remaining protected from hazardous sound levels. The communication device also enhances communication by extending the range within which users can communicate. Moreover, the communication device is unobtrusive and can be conveniently used during work, outdoor activity, or other physical activity. The communication device will be first described in connection with a hearing protection device, such as shown in FIGS. 1 and 2.

Figures 1, 2:
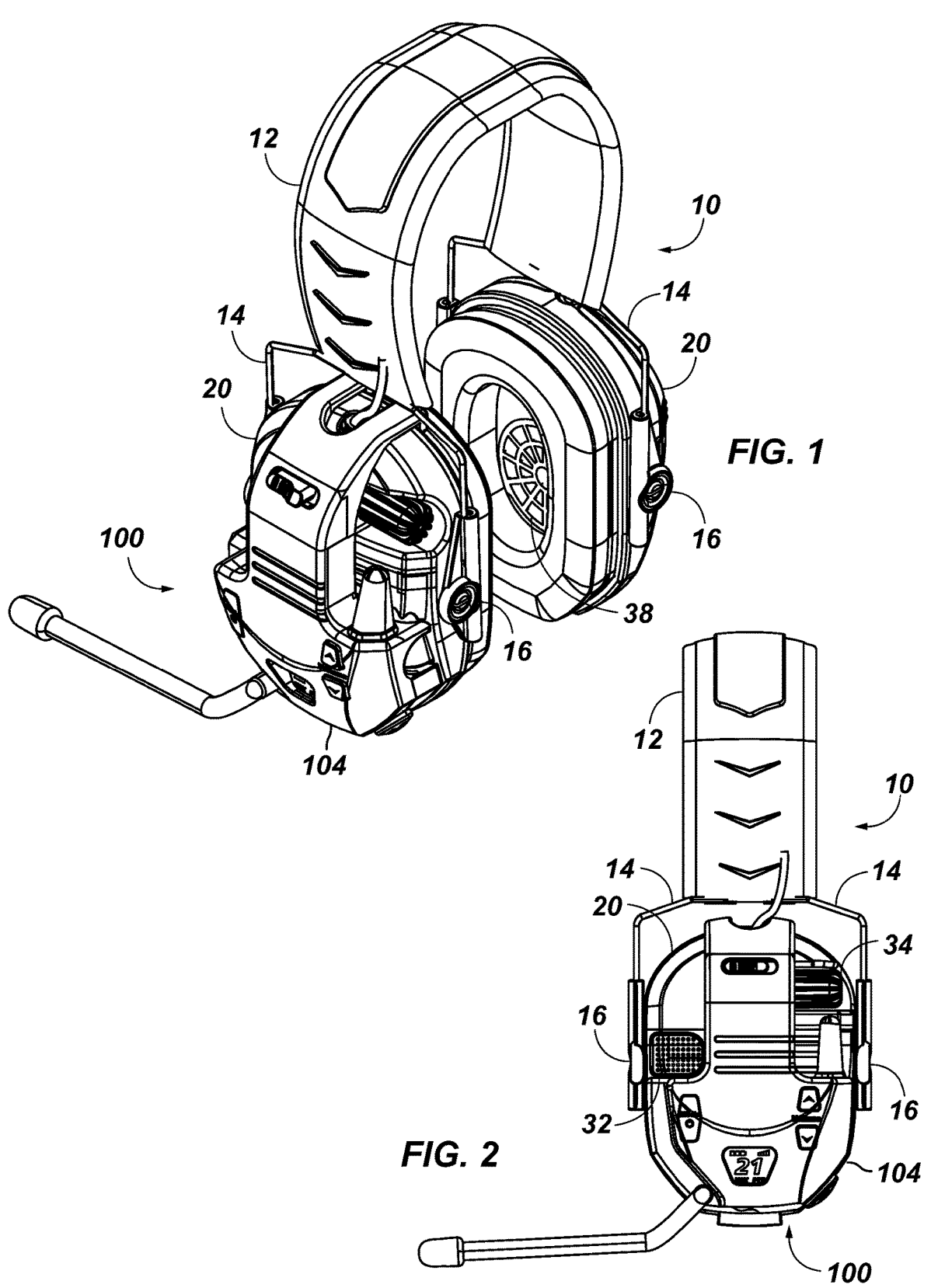
FIG. 1 is a perspective view of an exemplary communication device attached to a hearing protection device.
FIG. 2 is a side view of an exemplary communication device attached to a hearing protection device.

FIG. 1 illustrates an exemplary communication device 100 that is an independent device and has been attached to a hearing protection device 10 for use. As can be seen, a hearing protection device 10 may comprise an earmuff comprising a headband 12 and cups 20 that cover a user's ears. The cups 20 may be pivotally attached to the headband 12 by one or more pivoting mounts 16. In some embodiments, a pivoting mount 16 may comprise one or more arms 14.

The exemplary hearing protection device 10 of FIG. 1 features active noise cancellation via a speaker 38 in each of the cups 20. As shown in FIG. 2, a hearing protection device 10 may comprise one or more microphones 32 for active noise cancellation as well. In addition, one or more controls or input devices 34 may be provided, such as to adjust the volume at the speakers 38, turn on/off active noise cancellation, or control other functions of the hearing protection device.

Figures 3, 4, 5:
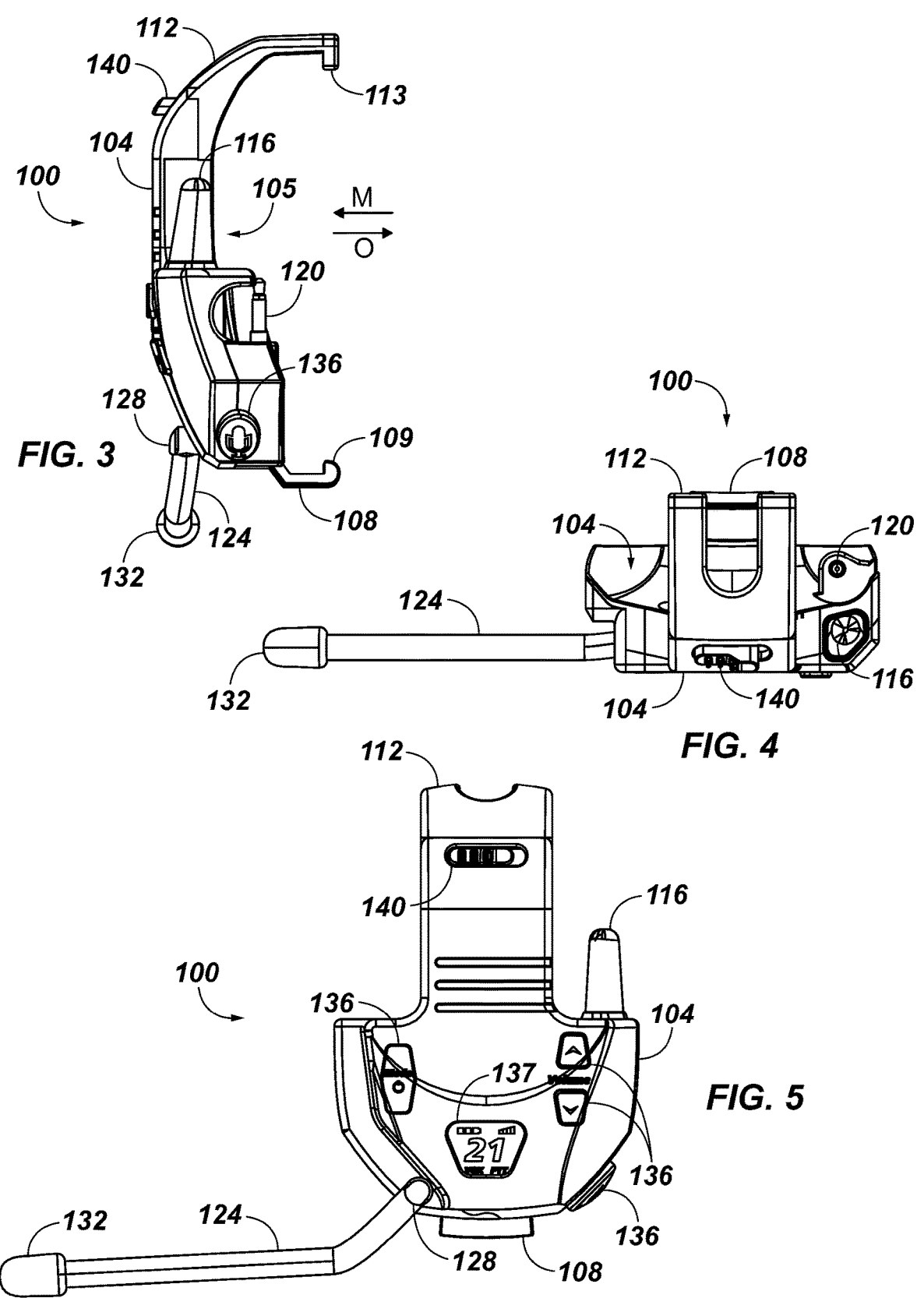
FIG. 3 is a side view of an exemplary communication device.
FIG. 4 is a top view of an exemplary communication device.
FIG. 5 is a front view of an exemplary communication device.

FIGS. 3 and 4 respectively illustrate side a top views of an exemplary communication device 100 and components thereof. A communication device 100 may comprise a housing or enclosure 104 that houses or supports various components of the communication device 100. An enclosure 104 will typically also facilitate removable attachment to a hearing protection device.

For instance, a communication device 100 may comprise one or more device mounts 108, 112 for removably attaching the communication device to a hearing protection device. As can be seen from FIG. 3, a device mount 108, 112 may be shaped to engage a hearing protection device to attach a communication device 100 thereto. In the embodiment of FIG. 3, for instance, the device mounts 108, 112 extend rearward from the enclosure 104 and comprise a projection 109, 113 at their distal ends that engage a cup of a hearing protection device.

A device mount 108, 112 may be a hook or hook shaped, like that shown, or may comprise other structures that facilitate removable attachment to a hearing protection device in one or more embodiments. It is noted that a device mount 108, 112 may be formed of a flexible or resilient material to aid in attachment to and removal from a hearing protection device, while an enclosure 104 remains rigid or at least more rigidly formed. One or more fasteners, such as screws, pins, or the like may be used to secure a communication device 100 in one or more embodiments.

As shown, a first device mount 108 is at a one end of the enclosure 104 while a second device mount is at an opposite end. Specifically, in the embodiment of FIG. 3, the first device mount 108 is at the bottom of the communication device 100 while the second device mount 112 is at the top. In such embodiments, one or more device mounts 108, 112 may engage a peripheral area of a cup to attach a communication device 100 thereto.

In some embodiments, an enclosure 104 may be shaped to receive a cup of a hearing protection device, such as to help secure a communication device 100. A back end 105 of an enclosure 104 may have an arcuate shape, such as to correspond to and receive a cup therein. As shown in FIG. 3 for instance, the back end 105 of the enclosure 104 has a concave shape.

One or more audio output connectors 120 will typically extend outward from an enclosure 104. The audio output connector 120 may provide an electrical, optical, or other type of physical connection through which signals may be transmitted to (or received from) a hearing protection device. In the exemplary embodiment of FIGS. 3 and 4, the audio output connector 120 comprises an electrical connector for communicating audio (or other) signals from the communication device 100 to a hearing protection device.

In one or more embodiments, an enclosure 104 and audio output connector 120 operate in conjunction to automatically connect to a hearing protection device when a communication device 100 is attached to the hearing protection device. Referring to FIG. 3, it can be seen that the enclosure 104 supports the audio output connector 120 at a particular location. This location is selected to align with a corresponding connector of a hearing protection device. In this case, the audio output connector 120 extends upright from a platform at a back end of the enclosure 104. When attached to a cup, the audio output connector 120 is automatically inserted into the corresponding connector at the cup, thereby allowing communication of audio signals therebetween.

A communication device 100 will typically include one or more recording devices, such as one or more microphones 132 to receive a user's voice or other audio. A microphone 132 may be mounted to an enclosure 104. In one or more embodiments, a boom or arm 124 may be provided to position the microphone 132 adjacent a user's mouth or otherwise at a position where the desired audio can be recorded. It is contemplated that a microphone 132 may be movable, such as via mounting on a pivot 128. An arm 124 may also or alternatively be bendable in some embodiments.

One or more antennas 116 will also be typically provided. An antenna 116 aids in transmission and reception of wireless signals to allow communication between multiple communication devices 100. Though shown as a particular antenna 116, it is contemplated that a variety of antennas 116, including internal antennas may be provided. In addition, it is contemplated that one or more antennas 116 may be connected to a communication device 100 via a cable. In this manner, an antenna 116 can be mounted to a hearing protection device or elsewhere, such as to improve signal transmission or reception.

One or more input devices 136 may be provided to receive user input. To illustrate, an input device 136 may be a button, switch, knob, touch screen, or other user input device. An input device 136 will typically be associated with a particular function. For example, as shown, an input device in the form of a switch is provided to turn the communication device 100 on and off. With reference to FIG. 5, which illustrates a front view of a communication device 100, a plurality of input devices 136 are provided to change channels, raise or lower volume, or activate a push to talk function.

One or more output devices 137 may be provided as well. An output device 137 generally provides feedback to a user. Some exemplary output devices 137 include display screens, vibrators, and speakers for instance. As shown in FIG. 5, the output device 137 comprises a screen that displays battery levels, volume information, and the current communications channel.

Figures 6A, 6B, 6C, 6D, 7:
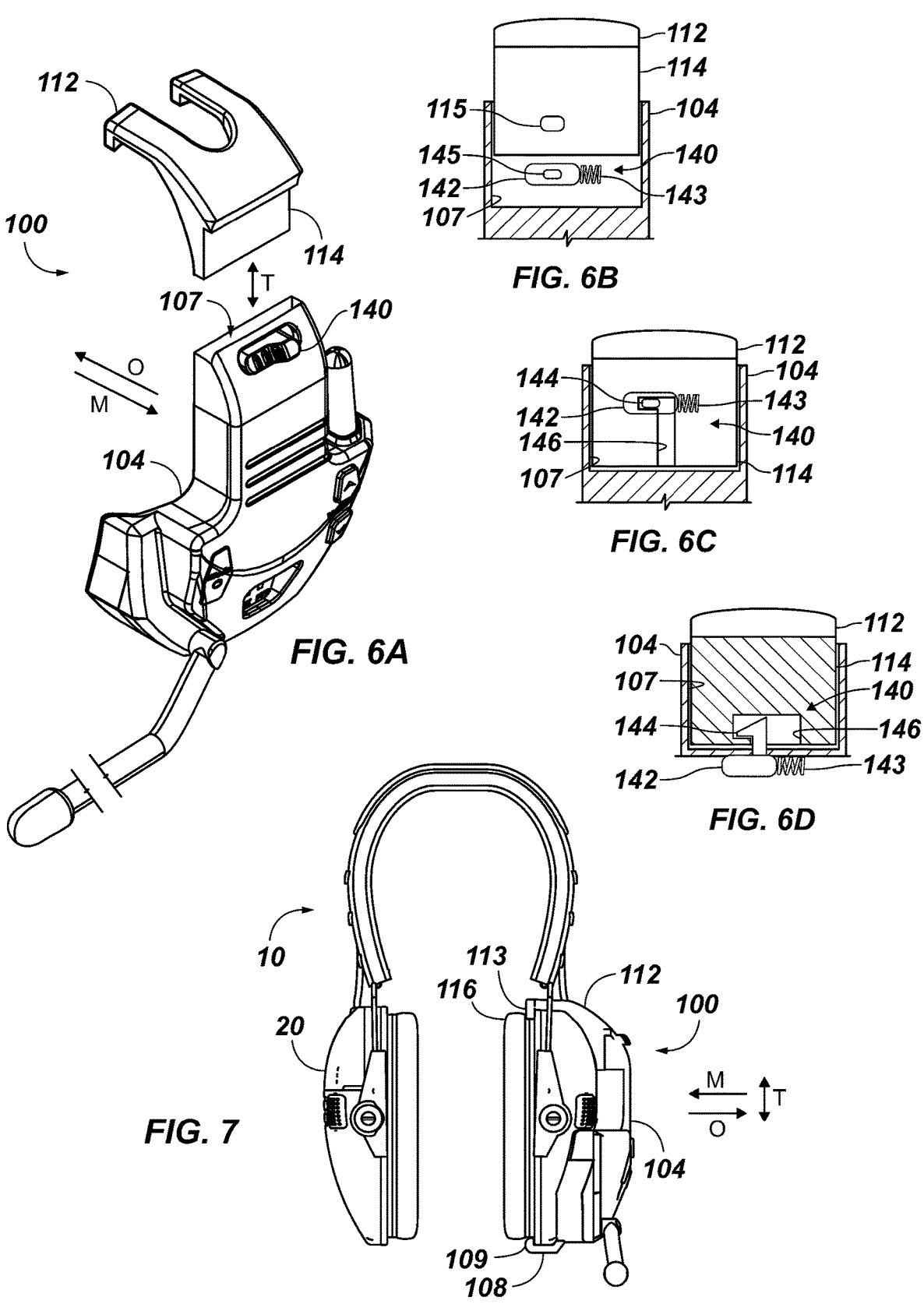
FIG. 6A is a perspective view of an exemplary communication device.
FIGS. 6B-6D are schematic view of latching or locking arrangements for the disclosed communication device.
FIG. 7 is a side view of an exemplary communication device attached to a hearing protection device.

FIGS. 6A-6D and 7 illustrate attachment and removal of a communication device 100 relative to a hearing protection device 10. As shown in FIG. 6A, one or more device mounts 112 may be removable to facilitate such attachment and removal.

For example, to attach a communication device 100, a first device mount 112 may first be removed, as shown in FIG. 6A. The back end of the enclosure 104 may then receive or engage a portion of the hearing protection device 10, such as a cup 20 of the hearing protection device, with a device mount 108 engaging a structure thereof, such as a lip, edge, or other portion of the cup. The other device mount 112 may then be reattached to the enclosure 104 while engaging the cup as well.

The communication device 100 is attached to the hearing protection device 10 in this manner, as shown in FIG. 7. As can be seen, a projection or hook 109, 113 of the device mounts 108, 112 engage the cup 20 in a transverse direction T, being transverse to a mounting direction M, to secure the communication device 100 thereto. As disclosed above, the attachment operation also connects an audio output connector (120) of the communications device 100 to the hearing protection device 10. In this state, the communication device 100 may be considered ready for use.

A device mount 112 may be made removable in various ways. Referring to FIG. 6A, a device mount 112 may be removable in a direction T, being transverse to a mounting direction M, via a tab or member 114 that is received within a corresponding groove, slot, or compartment 107. It is contemplated that various combinations of mating structures may be provided at the device mount 112 and enclosure 104. In addition, one or more fasteners, such as screws, pins, magnets, or the like, may be used to secure a device mount 112 in a removable fashion. In some the embodiments, a friction fit between the tab 114 and the compartment 107 can secure the device mount 112 to the enclosure 104.

As shown in FIGS. 6A-6D, a latch or lock 140 can be arranged between the enclosure 104 and the member 114 to latch/lock (engage) and unlatch/unlock (disengage) the device mount 112 to the enclosure 104. In an example, FIG. 6B shows a latch or lock 140 having a button or switch 142 biased by a spring 143 on the enclosure 104. The switch 142 can move a first magnetic element 145 relative to a second magnetic element 115 on the member 114 of the device mount 112, either latching the member 114 in the compartment 107 or allowing the member 114 to be inserted or removed linearly from the compartment 107. In another example, FIG. 6C shows a latch or lock 140 having a button or switch 142 biased by a spring 143. The switch 142 can move a key or node 144 in a profile, a slot, or the like 146 defined on the member 114 of the device mount 112, either latching the member 114 in the compartment 107 or allowing the member 114 to be inserted or removed linearly from the compartment 107. In yet another example, FIG. 6D shows another arrangement of a latch or lock 140 having a button or switch 142 biased by a spring 143. The switch 142 can move a key or hook 144 in a slot 146 defined on the member 114 of the device mount 112, either latching the member 114 in the compartment 107 or allowing the member 114 to be inserted or removed linearly from the compartment 107. Latch mechanisms having a bolt latch, a key and detent latch, a ball and detent latch, a sliding latch, a rotating latch, a magnetic latch, a cam latch, a snap-fit latch, and the like can also be used. These and other latch mechanisms can be used.

Removing a communication device 100 is generally a reverse procedure. In one or more embodiments, for example, one or more device mounts 108, 112 may be disengaged from the hearing protection device 10, and thereafter the communication device 100 may be removed. In the embodiment of FIGS. 6A-6D, the first device mount 112 may be removed from the enclosure 104, thereby disengaging the first device mount 112 from the hearing protection device's cup 20. Thereafter, the enclosure 104 and the remainder of the communication device 100 can be removed from the hearing protection device 10.

In some embodiments, device mounts 108, 112 need not be removable. As set forth above, a device mount 108, 112 may be flexible or resilient such as to allow malleability during attachment to and removal from a hearing protection device 10. To illustrate, one or more device mounts 108, 112 may be bent or otherwise manipulated when a cup 20 or other portion of a hearing protection device 10 is received or engaged by the enclosure 104 of a communication device 100 in a mounting direction M. A device mount 108, 112 can then be allowed returned to a normal or at rest state to secure a communication device 100 to a hearing protection device 10. Likewise, one or more device mounts 108, 112 can be bent or manipulated to allow a cup 20 to be disengaged from an enclosure 104 when removing the communication device 100 from a hearing protection device 10 in a direction O, being opposite to the mounting direction M. It is contemplated that one or more portions of an enclosure 104 may be formed of a resilient material to aid in attachment and removal as well.

Figure 8:
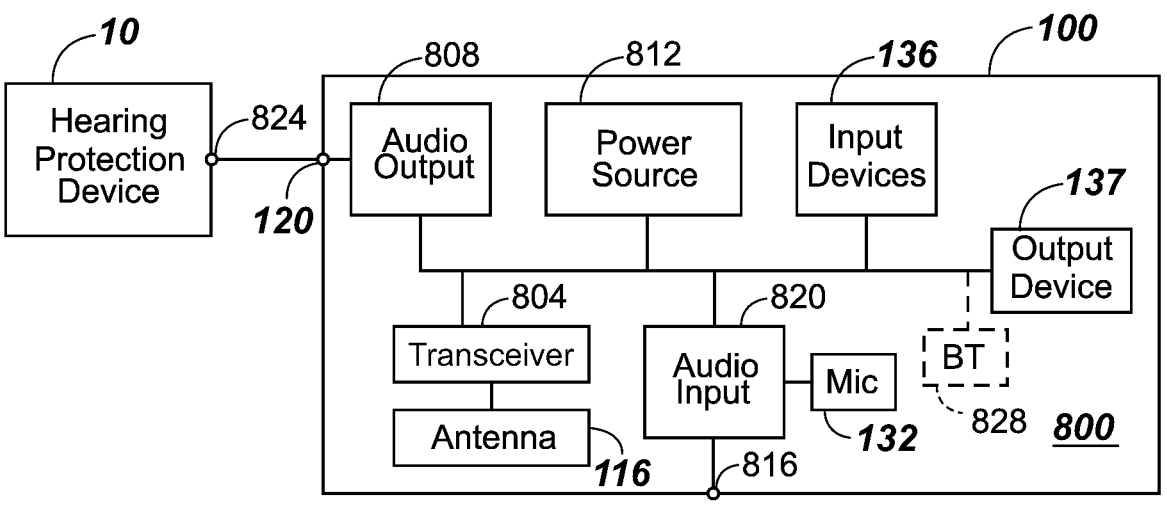
FIG. 8 is a block diagram illustrating components of an exemplary communication device.

FIG. 8 illustrates components of an exemplary audio communication circuitry 800 for a communication device 100 that is connected to a hearing protection device 10. Though shown as being connected via a bus, it will be understood that the components may be connected in various ways.

As can be seen, the audio communication circuitry 800 for the communication device 100 may comprise one or more radio transceivers 804, one or more power sources 812, one or more audio outputs 808, and one or more audio inputs 820. A power source 812 may comprise one or more batteries, solar panels, generator, or other device that is capable of providing power. A combination of various power sources 812 may be used in some embodiments. Some power sources 812 may be used to charge other power sources. Typically, a power source 812 will be portable, such as a battery.

A radio transceiver 804 may wirelessly transmit audio or other signals, receive such signals, or both. A radio transceiver 804 will typically be connected to one or more antennas 116 and may be capable of communicating wirelessly via one or more communication channels or frequencies, selectable by a user.

It is contemplated that one or more preset sounds or signals may be transmitted by a communication device 100. For example, prerecorded vocalizations, music, sounds, or the like may be transmitted upon engagement of a particular input device 136. A user may select from several preset sounds or signals in some embodiments, via one or more input devices 136. This provides particular information to other users depending on the transmitted sounds or signals and may be used for entertainment purposes as well. The preset sounds or signals may be recorded or stored on a storage device that is part of or connected to a radio transceiver 804.

Though disclosed above as a radio transceiver 804 capable of transmitting and receiving, it is contemplated that in some embodiments, only a radio transmitter or radio receiver may be provided for one-way or broadcast communication between communication devices 100. In addition, it is contemplated that communication devices 100 need not communicate via radiofrequency transmissions in the various embodiments of the present disclosure. For example, a communication device 100 may communicate optically via lasers, infrared, or other light signals in some embodiments. Accordingly, a variety of transceivers, including optical transceivers, may be utilized.

As disclosed above, a user's vocalizations and other local sounds may be received at an audio input 820. An audio input 820 will generally convert audio or sound into electrical signals and may receive such audio from one or more microphones 132. An audio input 820 may also or alternatively receive audio from another source via an audio input 816, which can be an audio or other type of connector.

For example, one or more independent microphones, or the audio output of another device may be connected via an audio input connector 816. A user may play music for instance through a smartphone or portable media player connected to the audio input connector 816. An audio input connector 816 may be an electrical, optical, or other connector. One or more cables may be used to connect external devices to an audio input connector 816.

The audio received at an audio input 820 will typically be transmitted to a radio transceiver 804 for transmission to other communication device 100. This may occur in an automated fashion or when a user engages a push to talk button input device 136 or the like. The same audio may optionally also be outputted via an audio output 808 so that a user can ultimately hear what is being captured or transmitted by their communication device 100.

An audio output 808 generally provides a signal, such as an electrical or optical signal, which can then be output to a user in audible form. Typically, an audio output 808 will receive at least the transmissions from a radio transceiver 804. These transmissions include remote audio, which is the transmitted audio from the communication devices 100 of other users. The audio output 808 then provides a corresponding signal to this remote audio as output.

As shown in FIG. 8, this output is received at a hearing protection device 10, when the hearing protection device is connected to the communication device 100. As disclosed above, the connection with a hearing protection device 10 may occur via one or more audio output connectors 120 of the communication device 100 that connect to a corresponding connector 824 of the hearing protection device.

It is contemplated that a length of cable (not shown) between an audio output connector 120 and an audio output 808 may be provided in some embodiments. This allows a communication device 100 to connect to a wide variety of hearing protection devices 10. It is contemplated that such cable (not shown) may be retractable in some embodiments.

Though described as an audio input 816 or audio output 808, it is contemplated that either component or both components may function as an input and output device for audio or other signals. For example, control signals for controlling volume or other functionality may be transmitted or received via an audio input 816 or audio output 808. Also, accordingly, an audio input and output may be a single combined component in some embodiments.

It is also contemplated that various wireless connections may be used in addition or instead of the audio inputs or connectors 816 and audio outputs or connectors 120 disclosed above. For example, a BLUETOOTH transceiver or other short-range wireless transceiver 828 may be provided to transmit and receive audio signals. In such embodiments, an audio input 820, audio output 808, or both may be connected to a short-range wireless transceiver 828 thereby reducing or eliminating the need for physical connections with a hearing protection device 10, external microphone, smartphone, or other external device.

As disclosed above, an output device 137 may present communication device status or configuration information, such as battery levels, volume, channel or frequency information, and other information.

Figure 9:
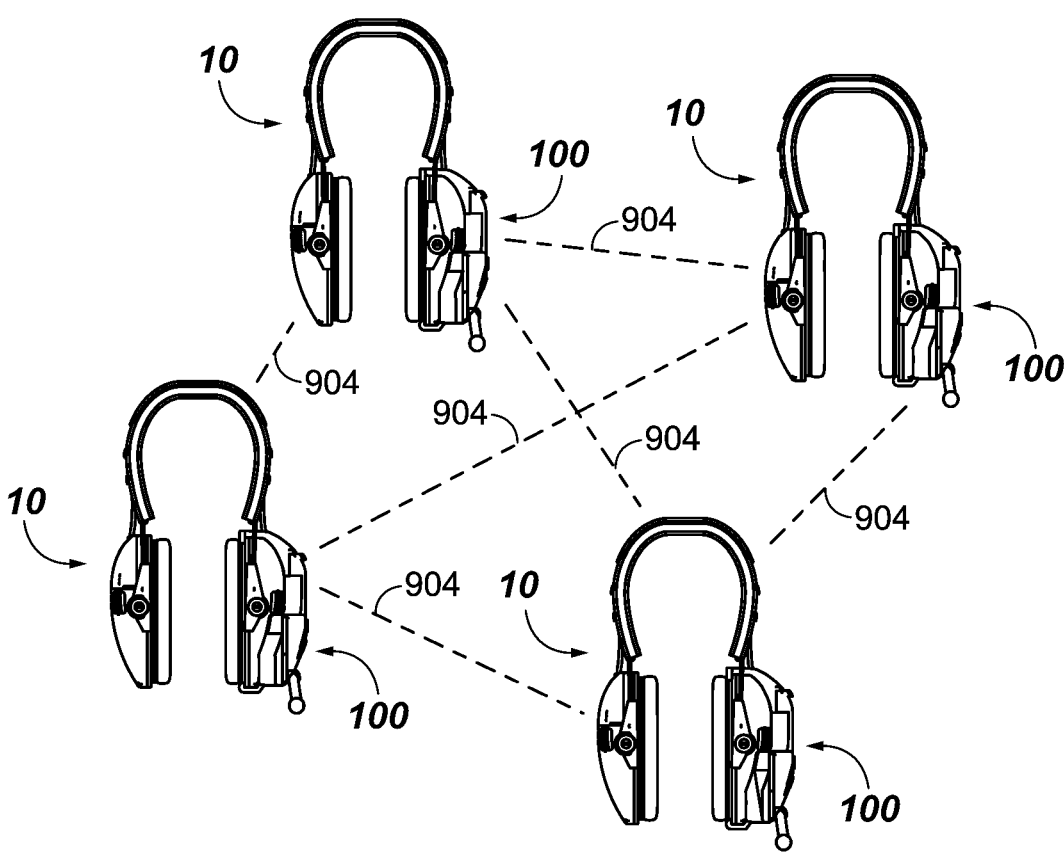
FIG. 9 illustrates exemplary communication devices in operation.

FIG. 9 illustrates a plurality of communication devices 100 in use. As can be seen, each communication device 100 has been attached to a hearing protection device 10. Accordingly, the corresponding users have their hearing protected via active attenuation provided by their hearing protection device 10. This is beneficial in reducing or eliminating the likelihood of hearing damage caused by firearm discharge, industrial noise, or other high decibel sounds. However, the ability for the users to communicate amongst one another is not limited. Instead, the users' ability to communicate is enhanced via the communication devices 100 attached to their hearing protection devices 10. Namely, each user can now communicate wirelessly in signals 904 across a distance while being audible despite the adornment of hearing protection devices by their peers.

As each user speaks, their voice is captured and transmitted in signals 904 from their communication device 100 to other communication devices 100. The receiving communication devices 100 output the user's voice via a speaker of the attached hearing protection device 10. While the hearing protection device 10 is actively attenuating harmful sounds, the output of a communication device 100 is passed through, allowing the same to be heard clearly. It is contemplated that, in some embodiments, an audio output 808 may change or alter the pitch, volume, or other characteristic of audio such that it is not attenuated by a user's particular hearing protection device 10.

As can be seen, the communication device 100 is highly beneficial to users that desire or require hearing protection and the ability to communicate easily without hinderance. This is quite often in hunting, shooting, industrial, or other environments with undesirable sound or noise levels.

Figure 10:
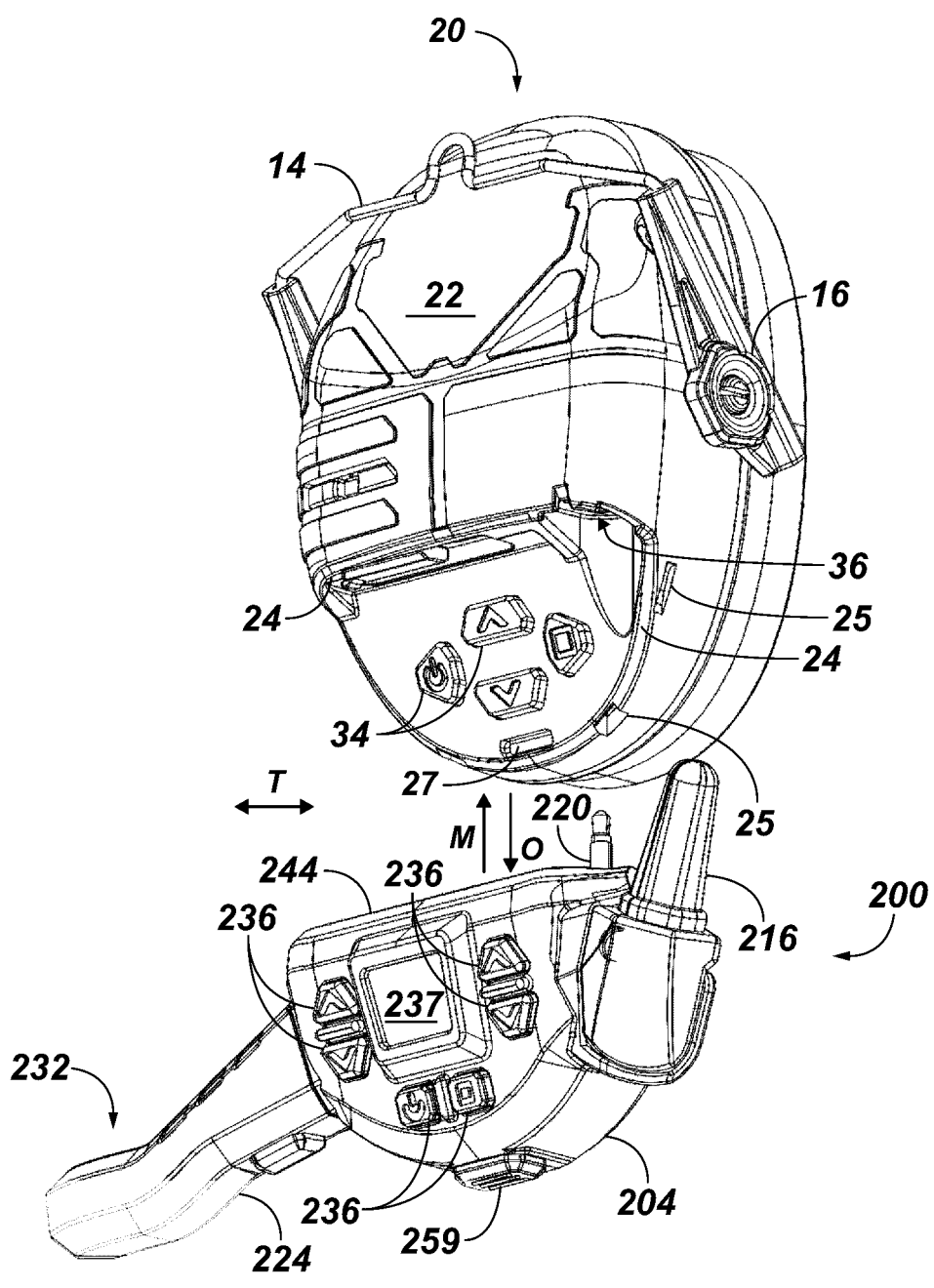
FIG. 10 is a front perspective view of an exemplary communication device and cup.

FIG. 10 illustrates another exemplary communication device 200 that may be removably secured to a hearing protection device. In FIG. 10, the communication device 200 is shown disengaged from a cup 20 of a hearing protection device (10).

Similar to above, the communication device 200 of FIG. 10 comprises one or more microphones 232, input devices 236, output devices 237, and connectors 220 housed or otherwise supported by an enclosure 204. An antenna 216 may be provided to facilitate wireless communication.

Also similar to above, a cup 20 may comprise an arm 14 and pivoting mount 16 for securing the cup to a hearing protection device. The cup 20 may comprise one or more input devices 34 for independently controlling the operation of the hearing protection device. Various ports 36 may be provided for connecting a cup 20 to a connector 220 of a communication device 200 for communication purposes. For example, input from one or more input devices 236 of a communication device 200 may be transmitted to a hearing protection device through a connector 220 and port 36, such as to allow such input to control aspects of the hearing protection device's operation.

Figure 11:
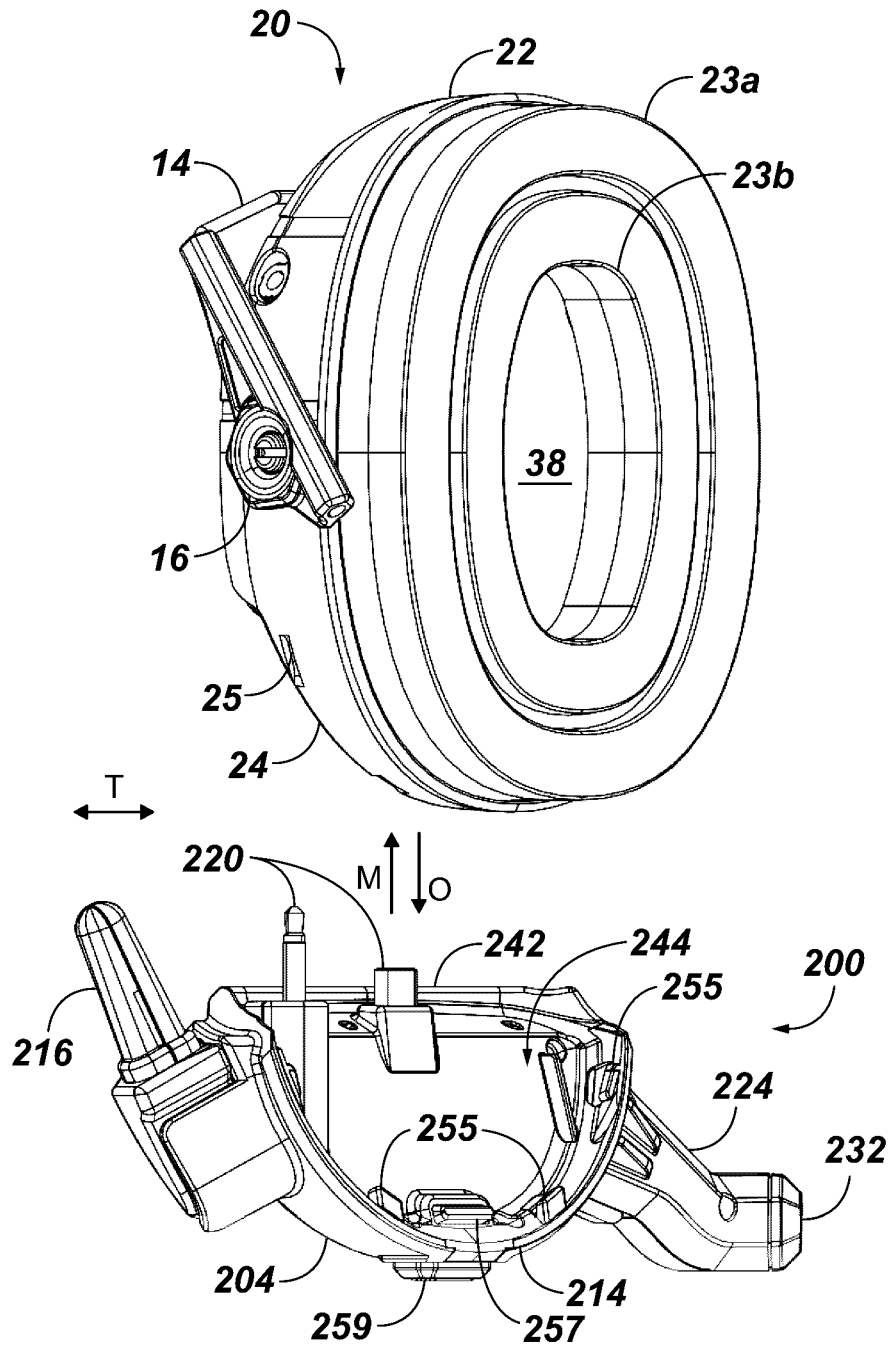
FIG. 11 is a back perspective view of an exemplary communication device and cup.

A cup's enclosure 22 will typically house or otherwise support various components of a cup 20 such as the previously described input devices 34 and ports 36. It is noted that a cup 20 may, in one or more embodiments, comprise a plurality of seals 23a, 23b to provide enhanced hearing protection. As shown in FIG. 11 for instance, the cup 20 comprises concentric seals 23a, 23b to provide enhanced hearing protection.

A communication device 200 may be removably secured to a hearing protection device in various ways. As described above, an enclosure 204 of a communication device 100 may be shaped to receive a cup 20 such as to allow the cup 20 to nest within the communication device's enclosure 204. As can be seen from FIGS. 11 and 12 (and FIG. 7 above), an enclosure 204 may have an open portion at its back end that receives a cup 20 therein when the communication device 200 is secured to the cup. A compartment 244 may be provided to receive a cup 20 in one or more embodiments.

Referring back to FIG. 10, an enclosure 204 of a communication device 200 may comprise one or more mating surfaces 242. A mating surface 242 of a communication device 200 may be an edge or other structure that engages a portion of a cup 20, such as at the cup's enclosure 22. A mating surface 242 of a communication device 200 may correspond in shape to a portion of a cup 20. In this manner, one or more mating surfaces 242 may form a friction fit or "click" fit to secure a communication device 200 to a cup 20, such as when the enclosure 204 receives the cup 20.

A cup 20 may also have one or more mating surfaces 24 that facilitate attachment of a communication device 200. A mating surface 24 of a cup 20 may be an edge or other structure that engages a communication device 200, such as at the communication device's enclosure 204. A mating surface 24 may be shaped to correspond to that of a device's enclosure 204, or portion thereof, to engage and secure the communication device 200 to the cup 20.

Figure 12:
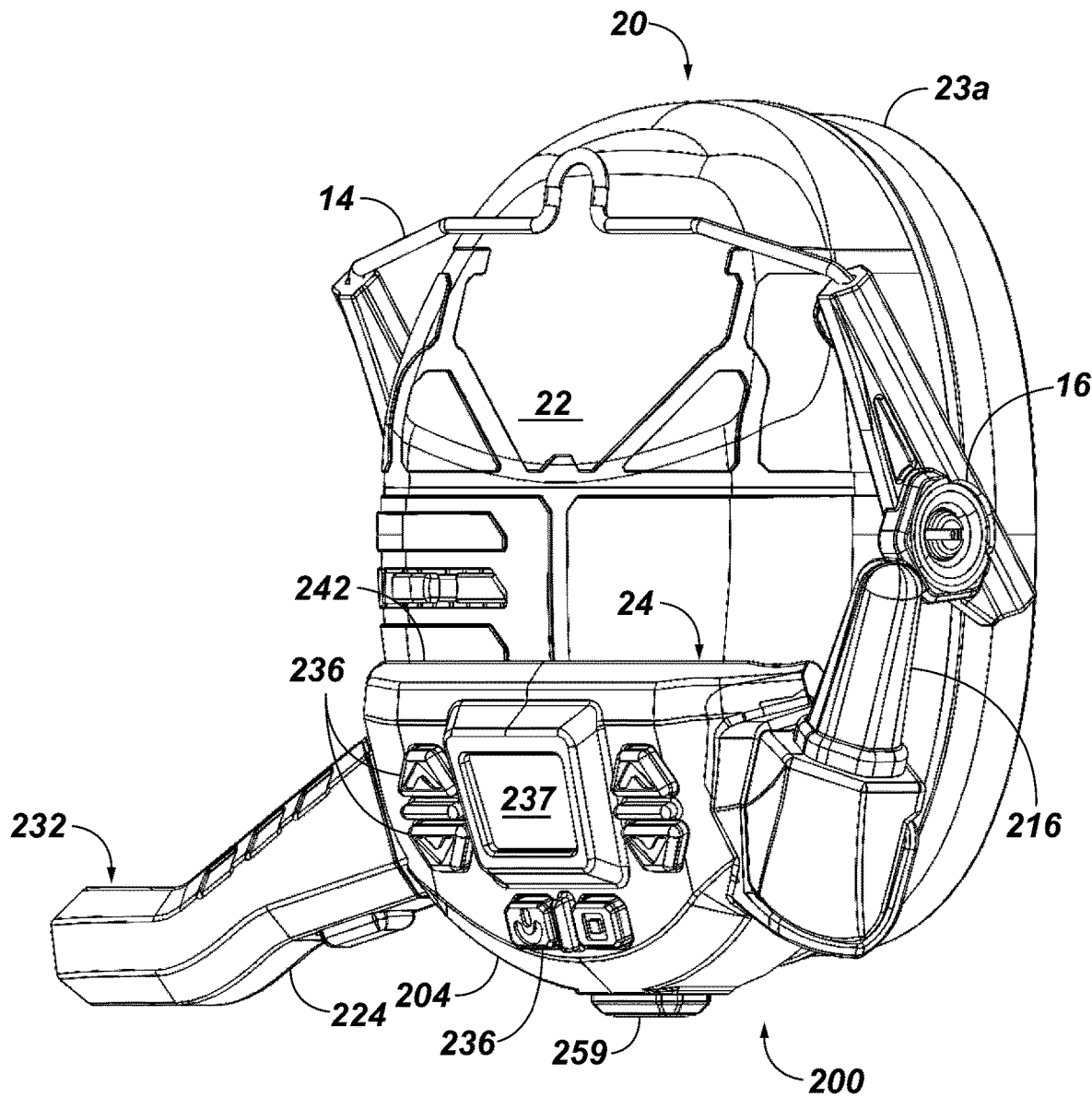
FIG. 12 is a perspective view of an exemplary communication device attached to a cup.

As can be seen in FIG. 12, mating surfaces 242, 24 may have corresponding contours and engage one another to secure a communication device 200. In addition, a mating surface 242 of a communication device 200 may also surround a correspondingly shaped portion of the cup 20. Referring to FIGS. 10 and 11, one or more slots 25 and 27, tabs 255 and 257, or other fasteners may also be provided to secure a communication device 200 when such fasteners are engaged to one another. One such slot 25 as shown in FIG. 10 can be provided on the cup 20 and can allow a tab 255 as shown in FIG. 11 extending on the communication device 200 to be inserted therein/connected thereto when engaging the enclosure 204 with the cup 20 in a mounting direction M and to be removed therefrom/disconnected therefrom when disengaging the enclosure 204 with the cup 20 in the opposite direction O to the mounting direction M.

Another slot 27 as shown in FIG. 10 can be provided on the cup 20 and can be engaged by a tab 257 as shown in FIG. 11 provided on the communication device 200. This tab 257 extends in a direction T, being transverse to the mounting direction M, to engage in the slot 27 when forming a "click" fit to secure the communication device 200 to the cup 20, such as when the enclosure 204 mounts on the cup 20 in the mounting direction M. A button 259 on the enclosure 204 can disengage the tab 257 from the slot 27 so the enclosure 204 can be removed from the cup 20 in the opposite direction O to the mounting direction D.

Figures 13A, 13B, 13C:
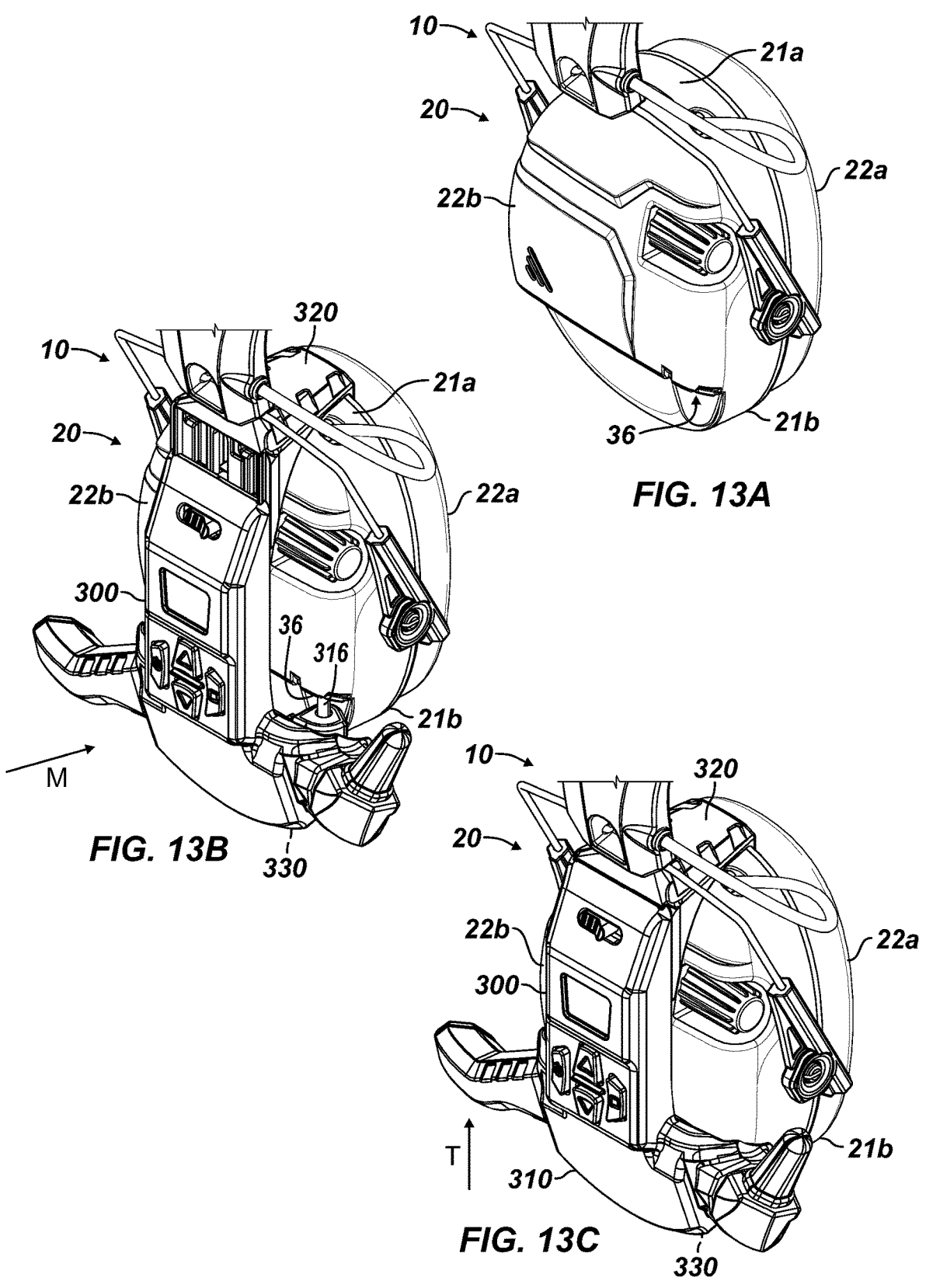
FIG. 13A illustrates a perspective view of an ear cup of a hearing protection device on which the disclosed communication device can be used.
FIG. 13B illustrates a perspective view of the disclosed communication device in the process of being installed on the ear cup of the hearing protection device.
FIG. 13C illustrates a perspective view of the disclosed communication device installed on the ear cup of the hearing protection device.

FIGS. 13A-13C illustrate perspective views of an ear cup 20 of a hearing protection device 10 on which another configuration of a communication device 300 of the present disclosure can be used. As shown in FIG. 13A, the hearing protection device 10 has an ear cup 20, having an electronic input 36, such as an audio input, and other electronic components. The cup 20 has an inner side 22a and an outer side 22b. The inner side 22a has a speaker (not shown), which is placed in electronic communication with the electronic input or connector 36 and with other elements of internal audio communication circuitry (e.g., 800 of FIG. 8).

As shown in FIG. 13B, the communication device 300 in an opened state is placed or mounted onto the outer side 22b of the cup 20. A mounting side of the communication device 300 position in a mounting direction (M) adjacent to the outer side 22b of the cup 20. A first mount or arm 320 on one end of the communication device 100 can be placed on an (upper) portion 21a of the cup 20. A second mount or arm 330 is spaced from another (lower) portion 21b of the cup 20.

A user then attaches the communication device 300 in a closed state onto the cup 20. An enclosure 310 of the device 300 can be moved in a transverse direction (T) to bring the arms 320, 330 of the communication device 300 against the upper and lower portions 21a-b of the cup 20. The arms 320, 330 are clamped onto the cup (e.g., by decreasing a dimension or distance between them, and the arm 320 is latched in place. One or more electrical connections are also made during the mounting process. For example, an electronic connector 316, such as an audio jack, on the communication device 300 is mated with the cup's electronic input 36.

The clamping and latching of the arms 320, 330 can be sufficient to hold the communication device 300 to the cup 20. Because the device 300 is used on a hearing protection device 10 worn on the head of a wearer, the attachment of the device 300 to the cup 20 is preferably secure enough to allow movement of the wearer without the device 300 inadvertently disengaging from the cup 20. The device 300 is detachable from the cup 20 by following a reverse process of its attachment.

Additional features discussed in previous embodiments can also be used to restrict movement of the communication device 300 on the cup 20 and to help hold the device 300 thereon. For instance, tabs (e.g., 255 and/or 257) can be used on the device 300, and slots (e.g., 25 and/or 27) can be used on the cup 20.

Figures 14A, 14B:
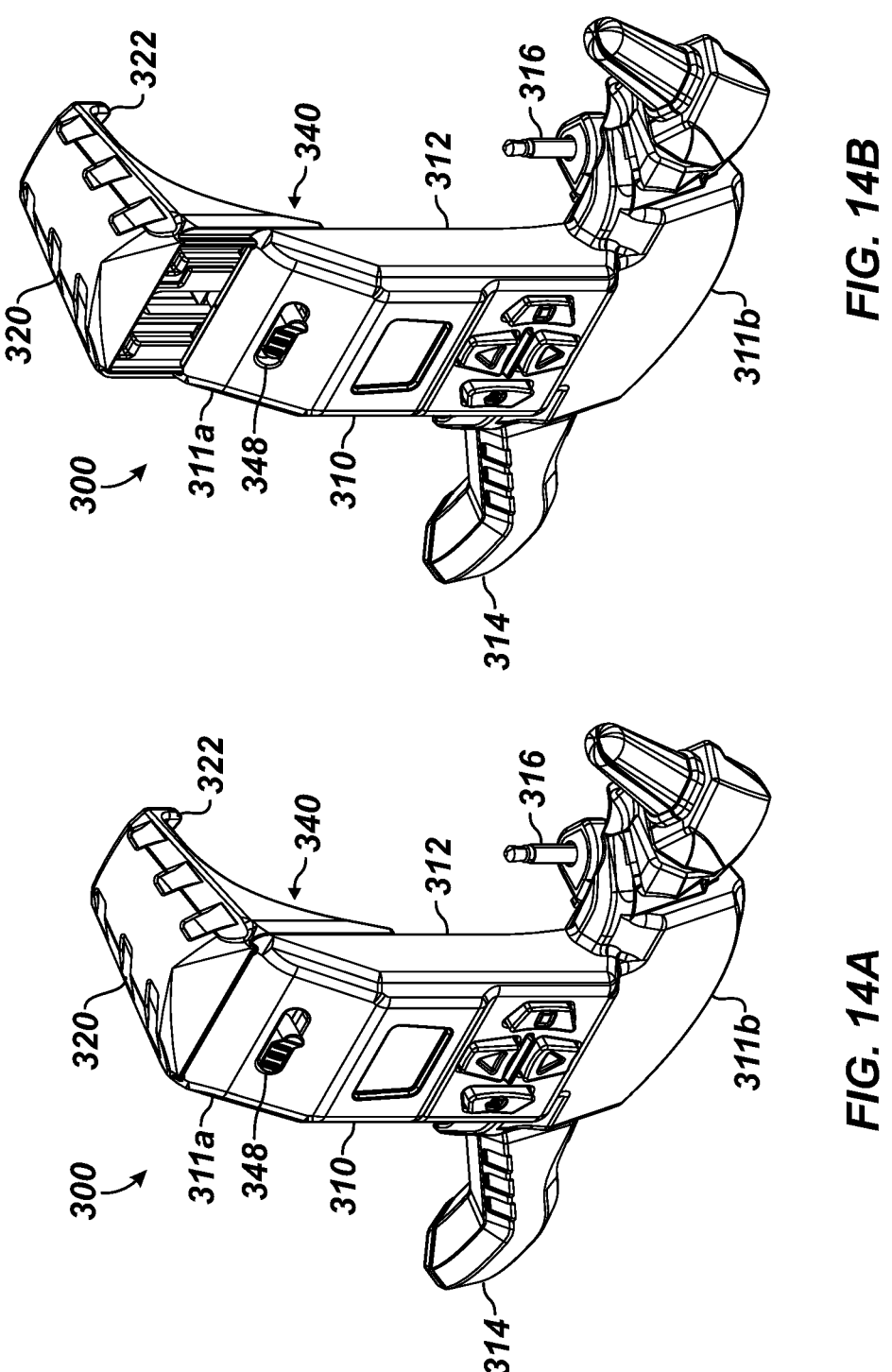
FIGS. 14A-14B illustrate perspective views of the disclosed communication device in respective first and second states.
Figures 15A, 15B:
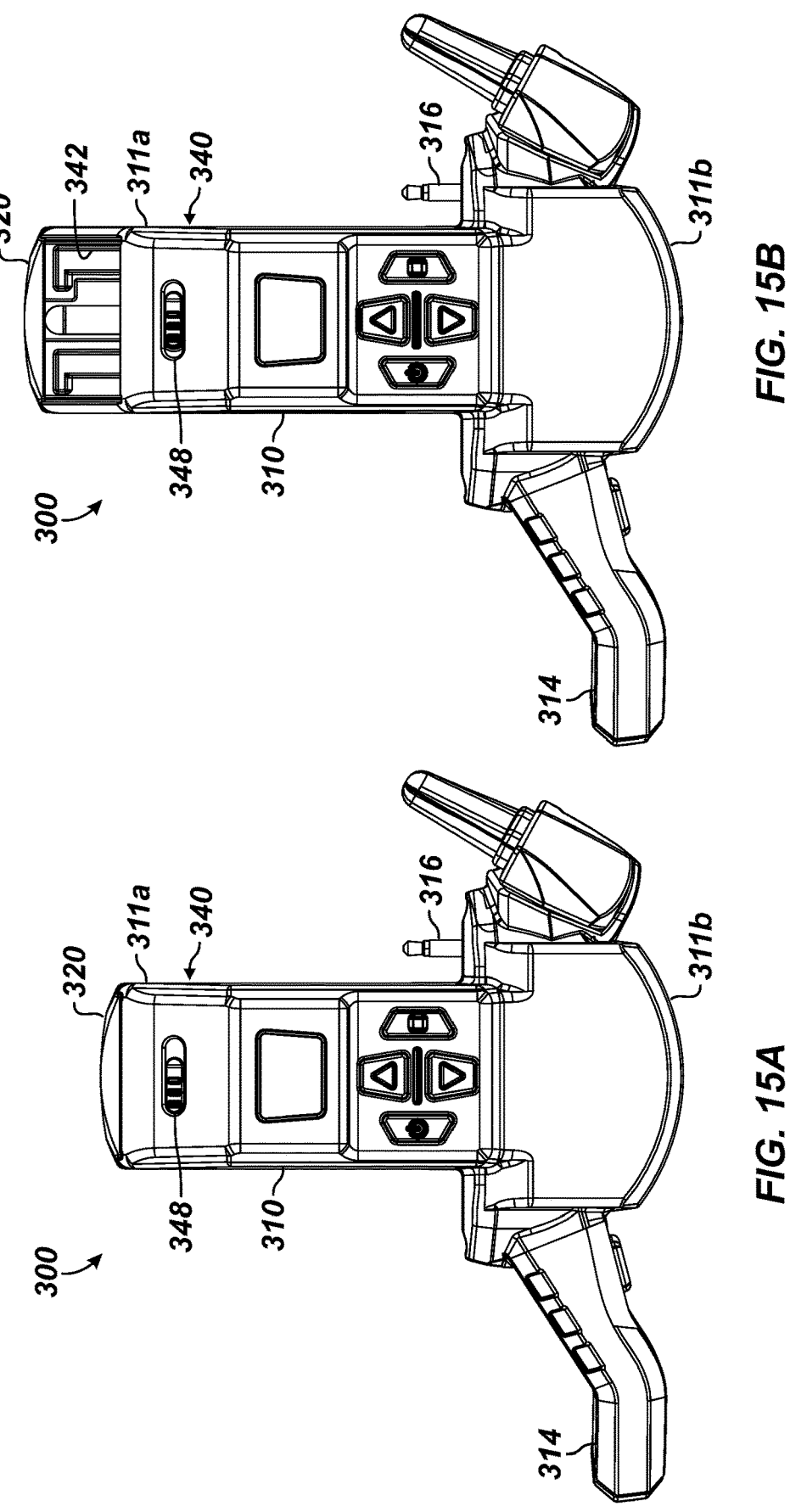
FIGS. 15A-15B illustrate views of an exterior side of the disclosed communication device in the respective first and second states.
Figure 16B:
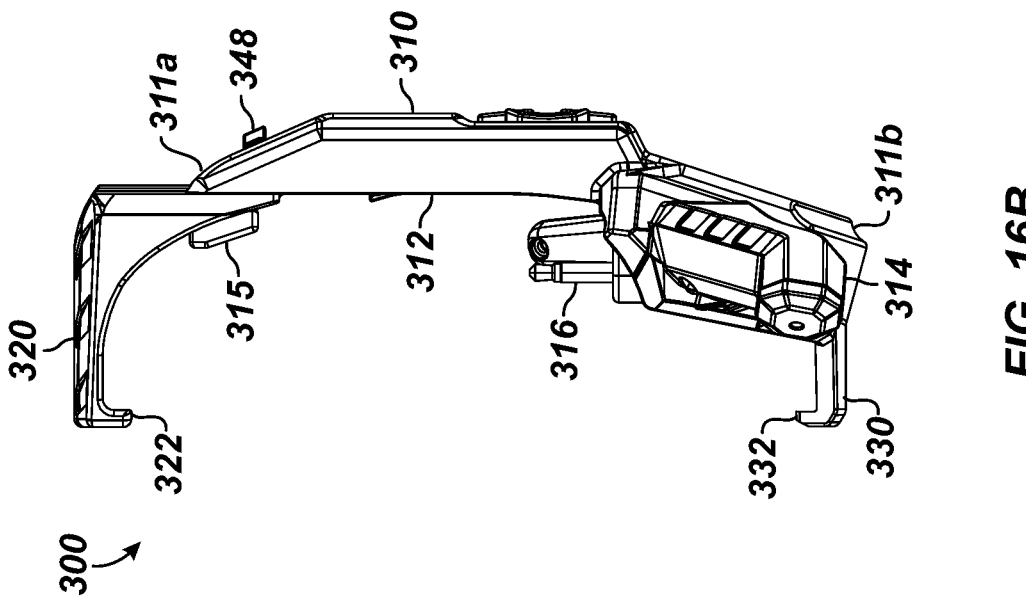
FIGS. 16A-16B illustrate front views of the disclosed communication device in the respective first and second states.
Figure 16A:
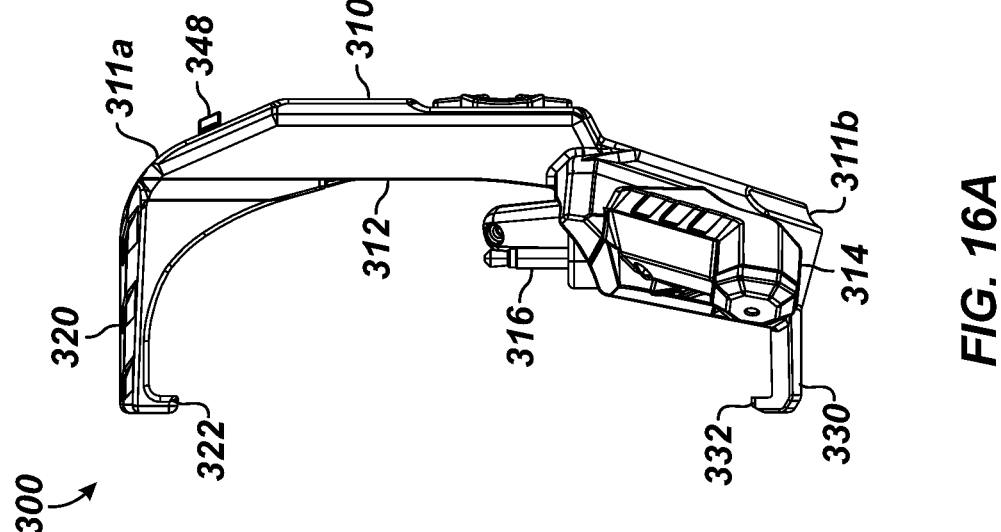
Figures 17A, 17B:
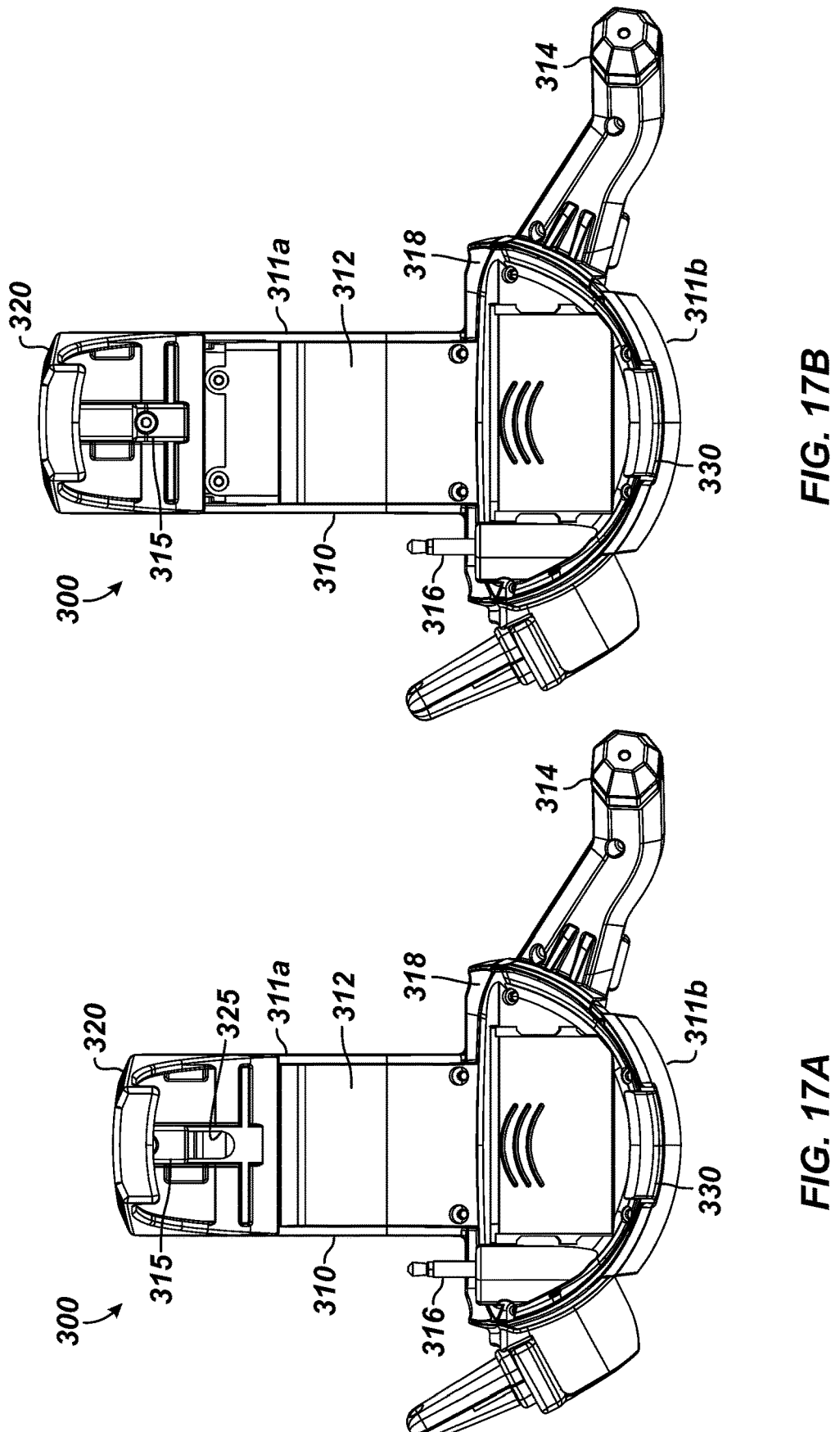
FIGS. 17A-17B illustrate views of an interior side of the disclosed communication device in the respective first and second states.

Looking at the communication device 300 in more detail, FIG. 14A through FIG. 17B illustrate various views of the disclosed communication device 100 in respective first and second states. For example, FIGS. 14A-14B illustrate perspective views of the disclosed communication device 300 in respective first (closed) and second (opened) states, and FIGS. 15A-15B illustrate views of an exterior side of the disclosed communication device 30 in the respective closed and opened states. Meanwhile, FIGS. 16A-16B illustrate front views of the disclosed communication device 300 in the respective closed and opened states, while FIGS. 17A-17B illustrate views of an interior side of the disclosed communication device 300 in the respective closed and opened states.

The communication device 300 includes an enclosure 310, a first mount or arm 320, and a second mount or arm 330. The enclosure 310 holds elements of audio communication circuitry (e.g., 800 of FIG. 8), which can include a microphone 314, a transceiver (not shown), antenna, one or more electronic outputs or connectors 316, etc. In general, the microphone 314 is configured to capture audio, and the electronic connector or output 316 is configured to connect to the audio input of the hearing protection device (10). The transceiver is in electronic communication with the microphone 314 and the electronic connector or output 316 and is configured to wirelessly transmit and receive wireless signals.

As best shown in FIGS. 14A-14B and 16A-16B, the enclosure 310 has a mounting side 312, a first end 311a, and a second end 311b. The mounting side 312 is configured to position adjacent to the outer side (22b) of the cup (20). The communication device 300 includes at least one electronic connector 316 disposed on the mounting side 312 of the enclosure 310. The electronic connector 316, which can be an audio jack or the like, is configured to connect to a corresponding input (36) on the hearing protection device

(10) when the mounting side 312 of the enclosure 310 is positioned adjacent to the outer side (22b) of the cup (20). The electronic connector 316 is configured to communicate one or more signals, including audio signals and other signals, between the communication device 300 and the hearing protection device (10).

As best shown in FIGS. 16A-16B, the first arm 320 is disposed toward the first (e.g., top) end 311a of the enclosure 310. The first arm 320 extends from the mounting side 312 of the enclosure 310 and is configured to mount to the first portion (e.g., top 21a) of the cup (20) in a first removable attachment. The first arm 320 is movable between first and second states relative to the enclosure 310. As hinted above, the first state corresponds to the first arm 320 positioned in a closed state moved down on the enclosure 310, whereas the second state corresponds to the first arm 320 positioned in an opened state moved upward on the enclosure 310. Preferably, the first arm 320 is movable but secured to the enclosure 310 so it is not necessary to install or remove the first arm 320 in order to mount or dismount the communication device 300 on the cup (20).

For its part, the second arm 330 is disposed toward the second (e.g., bottom) end 311b of the enclosure 310. The second arm 330 extends from the mounting side 312 of the enclosure 310 and is configured to mount to the second portion (e.g., bottom 21b) of the cup (20) in a second removable attachment.

As best shown in FIGS. 14A-14B, 16A-16B, and 17A-17B, the first and second arms 320, 330 each include a projection 322, 332 configured to engage the cup (20) in the respective first and second removable attachment. As noted previously, a mounting side 312 of the enclosure 310 is configured to position in a mounting direction adjacent to an outer side of a cup. The mounting side 312 defines a lip 318 thereabout, and the lip 318 is configured to engage the cup's outer side. When the communication device 300 is mounted to the cup (20), an external surface of the enclosure 310 can complete the outer side (22b) of the cup (20).

Although the first arm 320 is disposed toward a top end 311a of the enclosure 310 and the second arm 330 is disposed toward a bottom end 311b of the enclosure 310, a reverse arrangement can be used. The second arm 330 can be a fixed or a rigid component. In other configurations, the second arm 330 can be articulatable, such as being flexible or biased. As such, characteristics discussed above in other embodiments can be used for one or both of the arms 320, 330 of the present configuration.

Features related to movement of the first arm 320 are best shown in FIGS. 17A-17B. To support the movement of the first arm 320, the enclosure 310 includes a pin 315 toward the first end 311a, and the first arm 320 defines a slot 325 movable on the pin 315 of the enclosure 310. Other arrangements, such as a reverse pin and slot arrangement, can be used between the arm 320 and enclosure 310 that will permit sliding movement of the arm 320 relative to the enclosure 310. The arrangement of the pin 315 and the slot 325 can prevent removal of the first arm 320 from the enclosure 310. Additional guides and support features can be provided between the arm 320 and the enclosure 310 to facilitate stable movement.

As best shown in FIGS. 14A-14B and 15A-15B, the communication device 300 includes a latch or lock 340 disposed on the enclosure 310 toward the first (e.g., top) end 311a. The latch 340 is movable between first and second conditions. The latch 340 in the first (engaged) condition is configured to engage a latch profile 342 defined on the first arm 320 when the arm 320 is moved to the first and second (closed and opened) states. Meanwhile, the latch 340 in the second (disengaged) condition is configured to disengage from the latch profile 342, permitting movement of the arm 320 between the states.

The latch 340 includes a button 348 configured to move the latch 340 between the engaged and disengaged conditions. For example, the button 348 can slide back and forth to move the latch 340, although other mechanisms and motions can be used. Additional details related to the latch 340 are discussed below.

Figures 18A, 18B, 18C, 18D, 19, 20A, 20B:
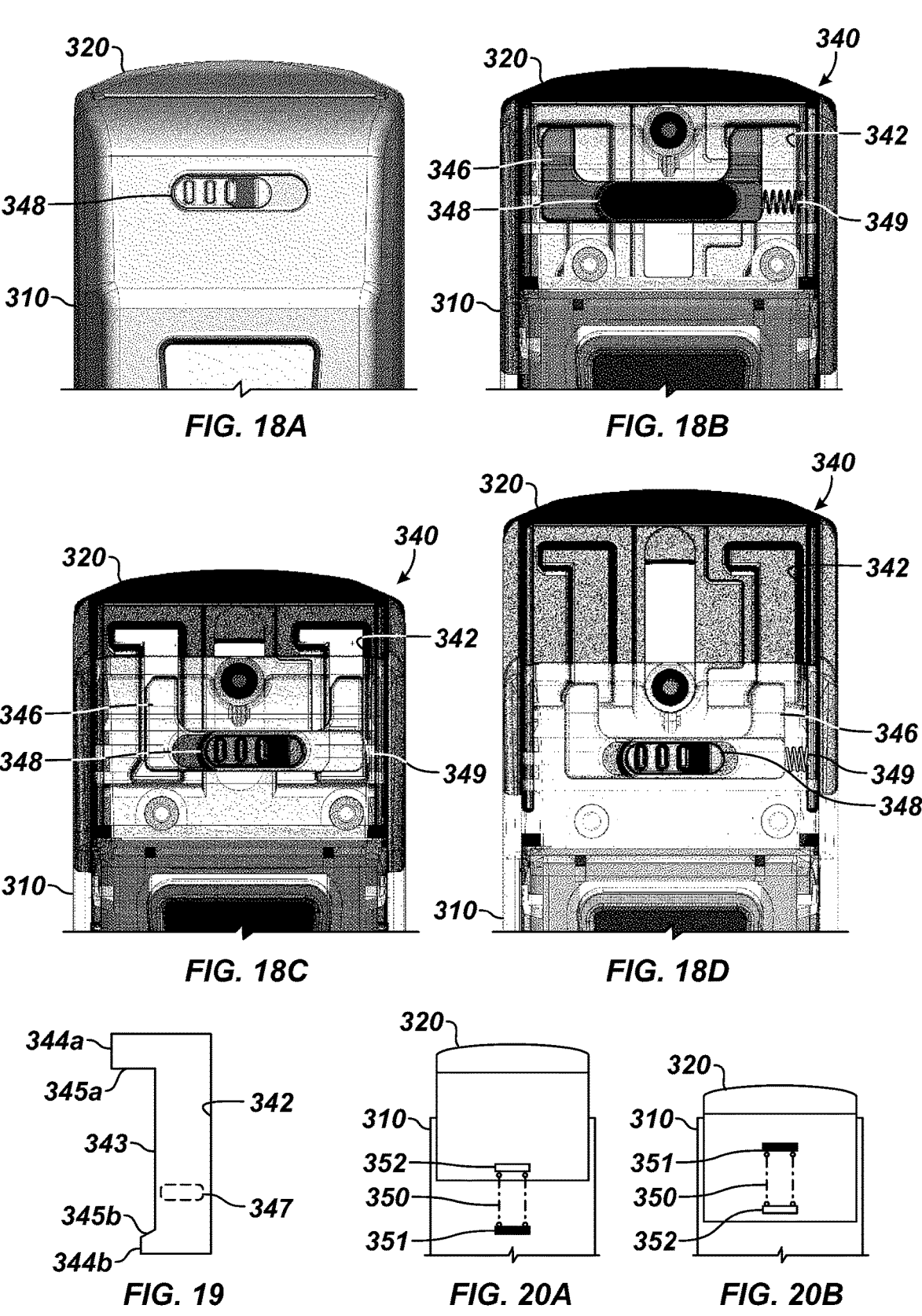

FIGS. 18A-18O illustrate schematic views of the function of the latch 340 and the first (clamping) arm 320 of the disclosed communication device 300, and FIG. 19 illustrates a schematic view of the latch profile 342 for the latch 340 the disclosed communication device 300.

In one configuration, the latch profile 342 includes first and second engageable portions or slots 344a-b. The first engageable portion 344a is a first lateral slot 344a toward one end of a longitudinal channel or slot 343, and the second engageable portion 344b is a second lateral slot 344b toward another end of the longitudinal channel 343. The first lateral slot 344a corresponds to the first (closed) state of the first arm 320, and the second lateral slot 344b corresponds to the second (opened) state of the first arm 320.

A portion of the latch 340 is movable in the latch profile 342. In particular, the latch 340 includes a plate 346, which is best shown in FIGS. 18B-18O. The plate 346 can be shifted by sliding of the button 348 affixed to the plate 346. As shown in FIG. 19, a key or head feature 347 on the plate 346 is movable in the latch profile 342. Notably and as shown in FIGS. 18B-18D, two adjacent latch profiles 342 and two key features (347) of the plate 346 can be provided for further support and stability.

To support the first arm 320 in its states, the first lateral slot 344a can define a first shoulder 345a being perpendicular to the longitudinal channel 343, and the second lateral slot 344b can define a second shoulder 345b being angled relative to the longitudinal channel 343. Additionally, the first lateral slot 344a can define a first lateral extent from the longitudinal channel 343, and the second lateral slot 344b can define a second (shorter) lateral extent from the longitudinal channel 343.

In one configuration, the latch 340 can be biased by a bias toward the first (engaged) condition. As shown in FIGS. 18B-18D, for example, the bias can be provided by a spring 349 or other biasing element, which is engaged against the plate 346. The spring 349 pushes the plate 346 so the key feature 347 can be engaged in the lateral slots 344a-b of the profile 342.

The first arm 320 in the second (opened) state can be movable toward the first (closed) state at least in response to a force overcoming the bias of the latch 340. For example, downward force on the first arm 320 can push the angled shoulder 345b against the latch's key feature 347, which shifts the latch's plate 346 against the bias of the spring 349. This can allow the first arm 320 to be pushed to its second (closed) state in which the key feature 347 aligns with the first lateral slot 344a and the spring 349 shifts the latch's plate 346 to a latched position. Any movement of the first arm 320 in an upward or longitudinal direction is then prevented by engagement of the key feature 347 with the perpendicular shoulder 345a of the latch profile 342 unless the latch 340 is moved to a disengaged condition.

In one configuration, the first arm 320 can be manually moved between its closed and opened states. For example, a user can move the first arm 320 when mounting and dismounting the communication device (300) on the cup (20) of a hearing protection device (10). With the first arm 320 in an opened state, for instance, the user can place the communication device 300 on the cup (20) and can push upward on the enclosure 310 so the electronic connector 316 inserts into the electronic input or audio port (36) on the cup (20), the lip 318 fits against the outer side (22b) of the cup (20), the second arm 330 fits toward the bottom (21b) of the cup (20), the first arm 320 moves to a closed state, and the latch 340 engages. A reverse process can be used to remove the communication device 300 from the cup (20).

In another configuration, the first arm 320 can be biased by a bias from the first (closed) state toward the second (opened) state. As shown in FIG. 20A, for example, the bias can be provided by a spring 350 or another biasing element. One end of the spring 350 can be engaged with a portion 351 disposed on the enclosure 310, and another end of the spring 350 can be engaged with a portion 352 disposed on the first arm 320.

In the arrangement of FIG. 20A, the spring 350 can be a compression spring and can push the portions 351, 352 apart so the arm 320 is biased from the closed state to the opened state (i.e., away from the enclosure 310). In this way, the latch 340 in the second condition disengaged from the latch profile 342 permits the first arm 320 to move by the bias from the closed state toward the opened state. This arrangement can facilitate removal of the communication device 300 from the cup (20).

In another arrangement of FIG. 20B, the spring 350 can be a compression spring and can push the portions 351, 352 apart so the arm 320 is biased from the opened state to the closed state. In this way, the latch 340 in the second condition disengaged from the latch profile 342 permits the first arm 320 to move by the bias from the opened state toward the closed state. This arrangement can facilitate attachment of the communication device 300 onto the cup (20). Of course, the spring 350 in either arrangement can be an extension spring, pulling the portions 351, 352 together and producing reversed operations.

Figures 21A, 21B:
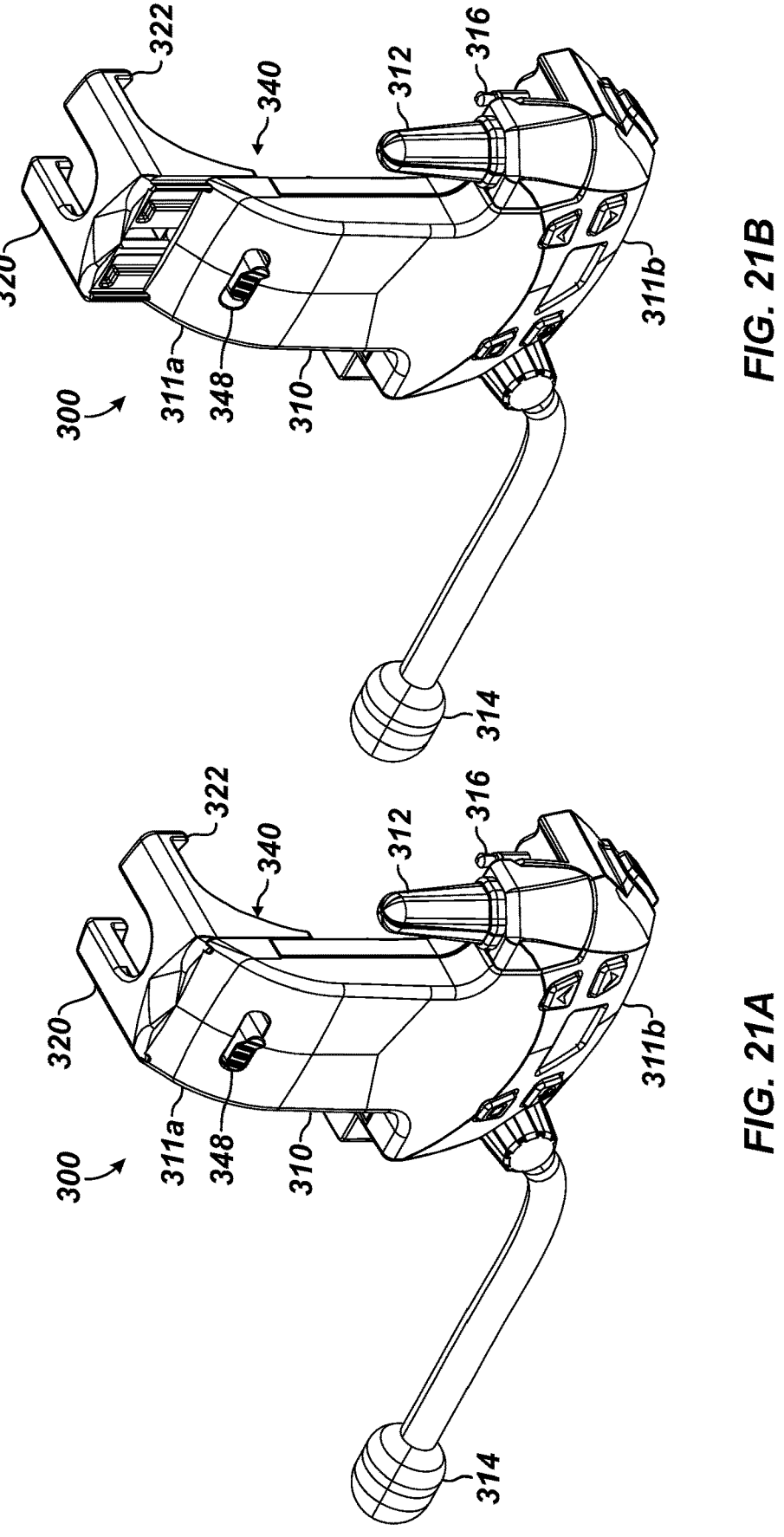
FIGS. 21A-21B illustrate perspective views of another communication device of the present disclosure in respective first and second states.

Finally, FIGS. 21A-21B illustrate perspective views of another communication device 300 of the present disclosure in respective first and second states. This communication device 300 can be used with a different type of cup for a hearing protection device. Nevertheless, this communication device 300 shares the many features of the previous configuration so the similar reference numerals are used. Discussion with respect to the configurations described above is reincorporated herein with respect to the communication device 300 of FIGS. 21A-21B.

While various embodiments of the present disclosure have been described, it will be apparent to those of ordinary skill in the art that many more embodiments and implementations are possible that are within the scope of the disclosed subject matter. In addition, the various features, elements, and embodiments described herein may be claimed or combined in any combination or arrangement.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter. In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A communication device for use with a hearing protection device, the hearing protection device having a cup and a first electronic connector, the cup having an inner side and an outer side, the outer side having first and second portions, the inner side having a speaker in electronic communication with the first electronic connector, the communication device comprising:

an enclosure having a mounting side, a first end, a second end, audio communication circuitry, and a second electronic connector, the mounting side being configured to position adjacent to the outer side of the cup, the audio communication circuitry in electronic communication with the second electronic connector, the second electronic connector being configured to connect to the first electronic connector of the hearing protection device;

a first arm disposed toward the first end of the enclosure, the first arm extending from the mounting side and being configured to mount to the first portion of the cup in a first removable attachment, the first arm being movable between first and second states relative to the enclosure;

a second arm disposed toward the second end of the enclosure, the second arm extending from the mounting side and being configured to mount to the second portion of the cup in a second removable attachment; and a latch arranged between the enclosure and the first arm and being movable between first and second conditions, the latch in the first condition being configured to engage the first arm in at least the first state, the latch in the second condition being configured to disengage from the first arm.

2. The communication device of claim 1, wherein the enclosure defines a compartment; and wherein a portion of the first arm is configured to removably fit in the compartment on the enclosure, whereby the first arm in the first state is attachable on the enclosure to extend from the mounting side of the enclosure and to engage with the first portion of the cup, and whereby the first arm in the second state is detachable from the enclosure to disengage from the first portion of the cup.

3. The communication device of claim 1, wherein the first arm is linearly movable relative to the enclosure in a first direction to decrease a dimension between the first arm and the second arm and in a second direction to increase the dimension.

4. The communication device of claim 1, wherein the latch in the first condition is configured to engage the first arm in the first state and in the second state, the latch in the second condition being configured to disengage from the first arm.

5. The communication device of claim 4, wherein the latch comprises a latch profile defined on the first arm, the latch in the first condition being configured to engage the latch profile of the first arm in the first state and the second state, the latch in the second condition being configured to disengage from the latch profile.

6. The communication device of claim 5, wherein the latch profile defines a longitudinal channel having a first lateral slot toward one end thereof and having a second lateral slot toward another end thereof, the first lateral slot corresponding to the first state of the first arm, the second lateral slot corresponding to the second state of the first arm; and wherein a portion of the latch is movable in the latch profile.

7. The communication device of claim 6, wherein at least one of:

the first lateral slot defines a first shoulder being perpendicular to the longitudinal channel, and the second lateral slot defines a second shoulder being angled relative to the longitudinal channel; and the first lateral slot defines a first lateral extent from the longitudinal channel, and the second lateral slot defines a second lateral extent from the longitudinal channel, the second lateral extent being less than the first lateral extent.

8. The communication device of claim 6, wherein the latch comprises a plate movable adjacent to the first arm; and wherein the portion of the latch movable in the latch profile comprises a key extending from the plate and disposed in the latch profile.

9. The communication device of claim 5, wherein at least one of:

the first arm is biased by a first bias from the first state toward the second state, whereby the latch in the second condition disengaged from the latch profile permits the first arm to move by the first bias from the first state toward the second state; and the first arm is biased by a second bias from the second state toward the first state, whereby the latch in the second condition disengaged from the latch profile permits the first arm to move by the second bias from the second state toward the first state.

10. The communication device of claim 4, wherein the latch is biased by a bias toward the first condition.

11. The communication device of claim 10, wherein the first arm in the second state is movable toward the first state at least in response to a force overcoming the bias of the latch.

12. The communication device of claim 1, wherein the audio communication circuitry comprises:

a microphone being configured to capture audio; and a transceiver in electronic communication with the microphone and the second electronic connector, the transceiver being configured to wirelessly transmit and receive wireless signals.

13. The communication device of claim 1, wherein the first arm is disposed toward a top end as the first end of the enclosure, and the second arm is disposed toward a bottom end as the second end of the enclosure; and wherein the first arm is configured to engage the cup toward a top end of the cup as the first portion, and the second arm is configured to engage the cup toward a bottom end of the cup as the second portion.

14. The communication device of claim 1, wherein each of the first and second arms comprises a projection configured to engage the cup in the respective first and second removable attachment.

15. The communication device of claim 1, wherein the enclosure comprises a pin toward the first end; and wherein the first arm defines a slot movable on the pin of the enclosure.

16. The communication device of claim 1, wherein the mounting side of the enclosure is configured to position in a mounting direction adjacent to the outer side of the cup; and wherein at least a portion of the mounting side defines a lip thereabout, the lip being configured to engage the outer side, whereby an external surface of the enclosure completes the outer side of the cup.

17. The communication device of claim 1, wherein the latch comprises a button configured to move the latch between the first and second conditions.

18. An assembly comprising:

a hearing protection device having a headband, a cup, and a first electronic connector, the cup having an inner side and an outer side, the outer side having first and second portions, the inner side having a speaker in electronic communication with the first electronic connector; and a communication device configured to removably mount on the cup, the communication device comprising:

an enclosure having a mounting side, a first end, a second end, audio communication circuitry, and a second electronic connector, the mounting side being configured to position adjacent to the outer side of the cup, the audio communication circuitry in electronic communication with the second electronic connector, the second electronic connector being configured to connect to the first electronic connector of the hearing protection device;

a first arm disposed toward the first end of the enclosure, the first arm extending from the mounting side and being configured to mount to the first portion of the cup in a first removable attachment, the first arm being movable between first and second states relative to the enclosure;

a second arm disposed toward the second end of the enclosure, the second arm extending from the mounting side and being configured to mount to the second portion of the cup in a second removable attachment; and a latch arranged between the enclosure and the first arm and being movable between first and second conditions, the latch in the first condition being configured to engage the first arm in at least the first state, the latch in the second condition being configured to disengage from the first arm.

19. A communication device for use with a hearing protection device, the hearing protection device having a cup and a first electronic connector, the cup having an inner side and an outer side, the outer side having first and second portions, the inner side having a speaker in electronic communication with the first electronic connector, the communication device comprising:

an enclosure having a mounting side, a first end, a second end, audio communication circuitry, and a second electronic connector, the mounting side being configured to position adjacent to the outer side of the cup, the audio communication circuitry in electronic communication with the second electronic connector, the second electronic connector being configured to connect to the first electronic connector of the hearing protection device;

a first arm disposed toward the first end of the enclosure, the first arm extending from the mounting side and being configured to mount to the first portion of the cup in a first removable attachment, the first arm defining first and second engageable slots, the first arm being movable between first and second states relative to the enclosure;

a second arm disposed toward the second end of the enclosure, the second arm extending from the mounting side and being configured to mount to the second portion of the cup in a second removable attachment; and a latch arranged between the enclosure and the first arm and being movable between first and second conditions, the latch having a key, the key on the latch in the first condition being configured to engage the first and second engageable slots of the first arm in the first and second states, the key on the latch in the second condition being configured to disengage from the first and second engageable slots of the first arm.

20. The communication device of claim 19, wherein the latch comprises a button configured to move the latch between the first and second conditions.

21. The communication device of claim 19, wherein the first arm defines a longitudinal channel having the first engageable slot extending laterally therefrom toward one end of the longitudinal channel and having the second engageable slot extending laterally therefrom toward another end of the longitudinal channel.

22. The communication device of claim 21, wherein at least one of:

the first engageable slot defines a first shoulder being perpendicular to a longitudinal direction of movement of the first arm, and the second engageable slot defines a second shoulder being angled relative to the longitudinal direction; and the first engageable slot defines a first lateral extent, and the second engageable slot defines a second lateral extent being less than the first lateral extent.

23. The communication device of claim 19, wherein the latch is biased by a bias toward the first condition.

24. The communication device of claim 23, wherein the first arm in the second state is movable toward the first state at least in response to a force overcoming the bias of the latch.

25. The communication device of claim 19, wherein at least one of:

the first arm is biased by a first bias from the first state toward the second state, whereby the latch in the second condition disengaged from the first and second engageable slots permits the first arm to move by the first bias from the first state toward the second state; and the first arm is biased by a second bias from the second state toward the first state, whereby the latch in the second condition disengaged from the first and second engageable slots permits the first arm to move by the second bias from the second state toward the first state.

* * * * *